United States Patent [19]

Fox

[11] 4,307,613

[45] Dec. 29, 1981

[54] ELECTRONICALLY FOCUSED ULTRASONIC TRANSMITTER

[75] Inventor: Martin D. Fox, Mansfield, Conn.

[73] Assignee: University of Connecticut, Storrs, Conn.

[21] Appl. No.: 48,699

[22] Filed: Jun. 14, 1979

[51] Int. Cl.³ .............................................. G01N 29/00
[52] U.S. Cl. ....................................... 73/626; 128/660; 367/105
[58] Field of Search ................. 73/626, 625, 628, 641; 367/103, 105, 122; 128/660

[56] References Cited

U.S. PATENT DOCUMENTS

| | | | |
|---|---|---|---|
| 3,616,682 | 11/1971 | Golis et al. | 73/641 |
| 3,886,488 | 5/1975 | Bossaert et al. | 73/603 |
| 3,895,339 | 7/1975 | Jones et al. | 367/7 |
| 3,971,962 | 7/1976 | Green | 73/641 |
| 3,979,711 | 9/1976 | Maginness et al. | 73/626 |
| 3,997,717 | 12/1976 | Mezrich et al. | 73/603 |
| 4,012,952 | 3/1977 | Dory | 73/626 |
| 4,058,003 | 11/1977 | Macovski | 73/626 |
| 4,063,549 | 12/1977 | Beretsky et al. | 128/660 |
| 4,064,741 | 12/1977 | Reynolds | 73/626 |
| 4,117,446 | 9/1978 | Alais | 73/628 |
| 4,219,846 | 8/1980 | Auphan | 73/626 |

OTHER PUBLICATIONS

S. A. Farnow et al., "An Acoustic Phase Plate Imaging Device", *Acoustical Holography*, vol. 6, pp. 259–273, 1975.

M. G. Maginness et al., "State-of-the-Art in Two Dimensional Ultrasonic Transducer Array Technology", *Medical Science*, No. 5, pp. 312–318, Sep.–Oct. 1976.

G. Kossoff, "Ultrasonic Two-Dimensional Visualization Techniques", IEEE Transactions on Sonic and Ultrasonics, pp. 31–37, June 1965.

P. Alais et al., "Fresnel Zone Focusing of Linear Arrays Applied to B and C Echography", *Acoustical Holography*, vol, 7, pp. 509–522, 1976.

*Primary Examiner*—Stephen A. Kreitman

[57] ABSTRACT

An array of transducer segments is arranged in columns, each of which has a multiplicity of segments. The segments are wired to permit excitation by one or the other of two opposite phases of high-frequency signal, and groups of segments can be excited with the same phase to approximate the shape of an annular-ring phase-reversal zone plate. By changing the groupings of the elements that are similarly excited, the position of the focal region produced by the zone plate is translated in lateral position. A ferrite-core transformer is conveniently employed for both phase splitting and addition of the echo signals received by the device.

13 Claims, 4 Drawing Figures

ELECTRONICALLY FOCUSED ULTRASONIC TRANSMITTER

BACKGROUND OF THE INVENTION

The present invention relates to ultrasonic transducer arrays. It is specifically directed to an electronic method of translating the focal region produced by a zone-plate array.

The past several years have witnessed a dramatic increase in the use of ultrasonic imaging in medical applications. It has become possible to view internal organs through the use of high-frequency acoustic waves that are introduced into the subject's body. The received echoes can give trained personnel a large amount of information without the necessity of employing X-rays. The use of ultrasonic imaging does not appear to be accompanied by the dangers that the use of X-rays has, and in some cases the information derived from acoustic imaging exceeds that obtained with X-rays.

Much of the work in acoustic imaging has been directed to focusing the acoustic energy. Focusing acoustic waves is similar in some respects to focusing light waves; acoustic lenses actually exist and have been used. However, acoustic waves appear also to lend themselves to focusing by means of constructive interference from discrete sources of acoustic energy. Acoustic energy is focused on a region if waves from a number of discrete sources constructively interfere in that region. Accordingly, if the relative phases of several sources can be adjusted so that they all arrive with the same phase at the desired point, acoustic focusing at that point has been achieved. This type of focusing naturally brings to mind the phased-array organizations employed in some sophisticated radar systems, and the phased-array organization has indeed found its way into the ultrasonic field. For instance, a linear array of transducers whose relative phases are controlled by tapped delay lines is described in an article by Maginness et al "State of the Art in Two-Dimensional Ultrasonic Transducer Array Technology," *Medical Physics*, September-October 1976, pp. 312-318. This type of arrangement is desirable in that it allows totally electronic focusing of the ultrasonic system. The same article also illustrates two-dimensional arrays, and the design and construction of such arrays is exemplified by the illustrated embodiment in U.S. Pat. No. 3,979,711 to Maginness et al.

Such arrays are quite desirable because the focusing is performed totally electronically, requiring no moving parts and allowing a scan rate that is rapid compared to the rates possible with mechanical focusing. However, they also tend to be somewhat expensive because a variable delay line must be provided for each of the elements of the array, and such delay lines are somewhat expensive particularly in quantity. Furthermore, a fair amount of information must be managed in such a system because the amount of delay required of each delay line must be stored. Furthermore, the typical phased-array arrangement often results in images that can be difficult to interpret because the resolution of the system varies with the distance to the focal region.

An arrangement that avoids some of these problems as described by Farnow and Auld in "An Acoustic Phase Plate Imaging Device," Acoustical Holography, Vol. 6, pp. 259-73 (N. Booth, ed., Plenum Press, 1975). This article describes the use of a Rayleigh-Wood phase-reversal zone plate in which concentric annular transducer elements are spaced so that the acoustic waves all constructively interfere at the desired focal point in which alternate elements are excited with opposite phases. Focusing in the depth direction is then accomplished by varying the frequency, which varies the distance to the point at which the ultrasonic waves from all the sources are in phase. This type of arrangement has two significant advantages. One is its tremendous simplicity as compared with the normal phased array. The second advantage is that the resolution achieved with this technique is substantially independent of the distance to the focal region. It can be appreciated that this is a great advantage for interpreting the images produced.

Accompanying the simplicity of the two-dimensional zone-plate arrangement, however, is the necessity for mechanically moving a two-dimension zone-plate transducer array if transverse motion of the focal region is desired. This is a significant drawback in comparison with the phased-array arrangement, particularly where real-time imaging is desired.

It is accordingly the object of the present invention to provide the simplicity, low cost, and uniform resolution of a zone-plate system while permitting transverse motion of the focal region to be accomplished electronically.

SUMMARY OF THE INVENTION

The foregoing and related objects are achieved in a novel electronically focused ultrasound transmitter that includes a transducer-element array. The array has first, second, third, and fourth generally circular groups of transducer elements. The first and second groups are being concentric and form a first zone-plate pattern, and the third and fourth groups are also concentric and form a second zone-plate pattern spaced from the first zone-plate pattern by a given directed distance. The first and third groups having no transducer elements in common with the second and fourth groups, respectively. The transmitter also includes signal generator means for generating first and second excitation signals of equal frequency and opposite phase and impressing the first and second excitation signals on the first and second output ports, respectively. There is a multiplicity of switch means, each of the switch means being electrically connected between one output port and at least one transducer element associated with the switch means. Each of the switch means is operable by application of control signals to it to connect and disconnect each transducer element associated with it to the output port to which it is connected. Finally, control circuit means are provided that are electrically connected to the switch means for application of control signals to them. The control-circuit means generate control signals and apply them to the switch means to simultaneously connect the first output port to the transducer elements of the first group and the second output port to the transducer elements of the second group, thereby focusing acoustic power from the transducer elements on a first focal region. The control circuit means then simultaneously connect the first output port to the transducer elements of one of the third and fourth groups and the second output port to the transducer elements of the other of the third and fourth groups thereby focusing acoustic energy on a second focal region spaced by the given directed distance from the first focal region.

The transducer elements can conveniently be arranged in mutually perpendicular rows and columns, each column including transducer elements whose dimensions in the direction of the column vary generally in a zone-plate progression. Each row includes transducer elements of substantially equal dimensions in the direction of the columns. The third group of transducer elements consists of each transducer element that is disposed a predetermined number of transducer elements in a given direction along its row from a transducer element of the first group, and the fourth group of transducer elements consists of each transducer element that is disposed the predetermined number of transducer elements in the given direction along its row from a transducer element of the second group.

In the preferred embodiment, each of the columns includes a central transducer element and a plurality of pairs of other transducer elements. Each pair is spaced symmetrically about the central transducer element, and each switch electrically connected to one transducer element of a symmetrically spaced pair is also electrically connected to the other transducer element of the same pair. Transducer elements of a symmetrical pair are thereby driven by the same excitation signal.

Typically, each of at least some of the transducer elements is electrically connected to two of the switch means, one of which is electrically connected to the first output port, the other of which is electrically connected to the second output port, for alternate driving by either of the excitation signals.

In a convenient arrangement, there are seven rows of transducer elements, each row including a central transducer element and three pairs of other transducer elements, each pair being arranged symmetrically about the central transducer element.

The signal generator means may conveniently include a transformer having primary and center-tapped secondary windings. An oscillator would be connected across the primary windings for application of a signal having the desired excitation frequency, and the secondary windings would be grounded at the center tap and to provide the first and second output ports at opposite ends of the secondary windings. Preferably, the transformer is a ferrite-core transformer.

Transmission circuit means would ordinarily be electrically connected to the primary windings for reception of signals present on them. The transmission circuit means would be adapted for electrical connection to display means and operable by application of control signals thereto when electrically connected to the display means to alternately apply to and withhold from the display means signals from the primary windings. The signal generator means would be operable by application of control signals thereto to alternately apply to and withhold from the transformer primary windings signals from the oscillator. The control circuit means would be electrically connected to the signal generator means and the transmission circuit means for application of signals to them and would include means for applying control signals to the transmission circuit means and the signal generator means to alternately operate the signal generator means to apply the oscillator signal to the primary windings while operating the transmission circuit means to withhold the signal on the primary windings from the display means and operate the transmission circuit means to apply the signal on the primary windings to the display means while operating the signal generator means to withhold from the primary windings signals from the oscillator.

In the normal arrangement, some of the transducer elements included in the third or fourth group are also included in the first or second group.

Broadly defined, the present invention can be embodied in any device that includes a transducer-element array as previously described, signal generator means, including at least one output port, for generating and impressing upon each output port an excitation signal associated with the output port, each excitation signal having the same frequency, a multiplicity of switch means, each switch means being electrically connected between one output port and at least one transducer element associated with the switch means and being operable by application of control signals thereto to connect and disconnect each transducer element associated with it to the output port to which it is connected; and control circuit means, electrically connected to the switch means for application of control signals. The control circuit means generates control signals and applies them to the switch means to simultaneously connect an output port to the transducer elements of the first group and an output port to the transducer elements of the second group, thereby focusing acoustic power from the transducer elements on a first focal region, and subsequently to simultaneously connect an output port to the transducer elements of the third group and an output port to the transducer elements of the fourth group, thereby focusing acoustic power on a second focal region spaced by the given directed distance from the first focal region.

A method of electronically focusing acoustic power is also taught that includes the steps of providing a transducer-element array including first, second, third, and fourth generally circular groups of transducer elements, the first and second groups being concentric and forming a first zone-plate pattern, the third and fourth groups being concentric and forming a second zone-plate pattern spaced from the first zone-plate pattern by a given directed distance, the third and fourth groups having no transducer elements in common with the first and second groups, respectively, simultaneously driving the first group with a first excitation signal and the second group with a second excitation signal equal in frequency to the first excitation signal but opposite in phase, thereby concentrating acoustic power on a first focal region, and subsequently driving the third group with one of the excitation signals and the fourth group with the other of the excitation signals, thereby concentrating acoustic power on a second focal region spaced by the given directed distance from the first focal region.

BRIEF DESCRIPTION OF THE DRAWINGS

These and further features and advantages of the present invention are described with reference to the attached drawings, in which.

DETAILED DESCRIPTION OF THE PREFERRED EMBODIMENT

Figure 1:
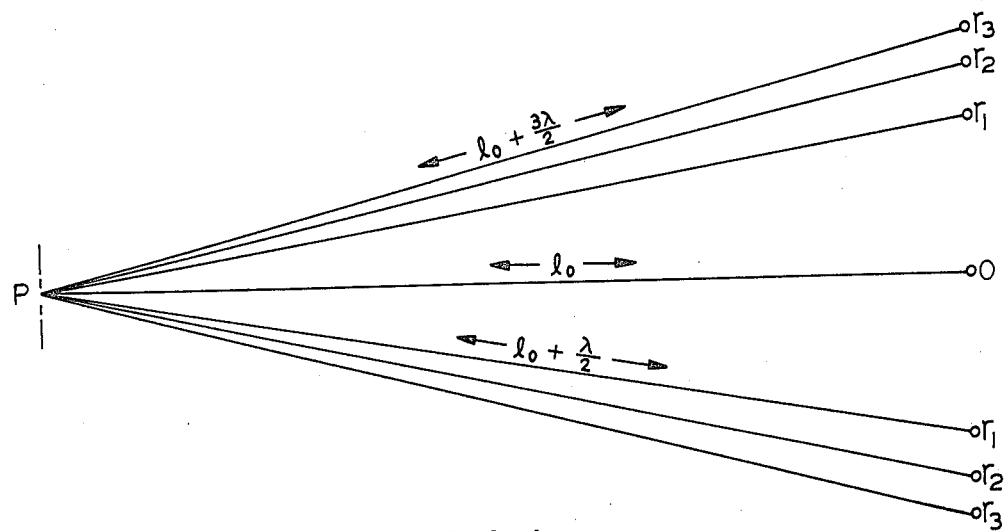
FIG. 1 is a diagram illustrating the geometry on which the zone plates are based.

The geometry for a zone plate, which focuses a major part of the power from a group of wave sources on a small region, is illustrated in FIG. 1. The focusing is accomplished by causing the waves from all of the sources to constructively interfere at the focal point P. A central source is spaced from point P by a length $l_o$, and each of the other sources is spaced from point P by a distance that differs from $l_o$ in a phase-reversal zone plate by an integral number of half wavelengths:

$$l_n = l_o + \frac{n\lambda}{2}, \qquad (1)$$

where n is a positive integer, $l_n$ is the length to point P from either nth source, and $\lambda$ is the wavelength. With this spacing, wave energy from the various point sources will constructively interfere at point P. If every other source is in phase and the alternate sources differ by full wavelengths, all sources can be excited with the same phase.

In the characteristic zone-plate spacing, the distance of the nth source from the central source usually increases approximately as the square root of n. Applying the Pythagorean Theorem to FIG. 1, $$r_n^2 + l_o^2 = \left(l_o + \frac{n\lambda}{2}\right)^2 \qquad (2)$$

or $$r_n^2 = nl_o\lambda + \frac{n^2\lambda^2}{4}, \qquad (3)$$

where $r_n$ is the distance from the central source to the nth source. For present purposes, it can be assumed that the distance between the central source and the focal point is much greater than n wavelengths, or $$l_o \gg n\lambda, \qquad (4)$$

so $$r_n \cong \sqrt{nl_o\lambda}$$

A phase-reversal zone-plate array therefore normally has a spacing that approximates the relationship given in equation (4), and it will be appreciated that the ratios between the $r_n$'s will be the same for zone plates whose sources are all intended to have the same phase. In fact, these ratios would hold for any such arrangement in which each source differed in phase from the heat lower-numbered source by the same constant amount. Of course, the foregoing derivation assumes that the sources all lie on a straight line (or, as will be seen below, a common plane); if they did not, the spacing would, of course, be somewhat different, but the principle would still be the same; the spacing should be arranged so that all of the sources constructively interfere at the desired focal point.

Figure 2:
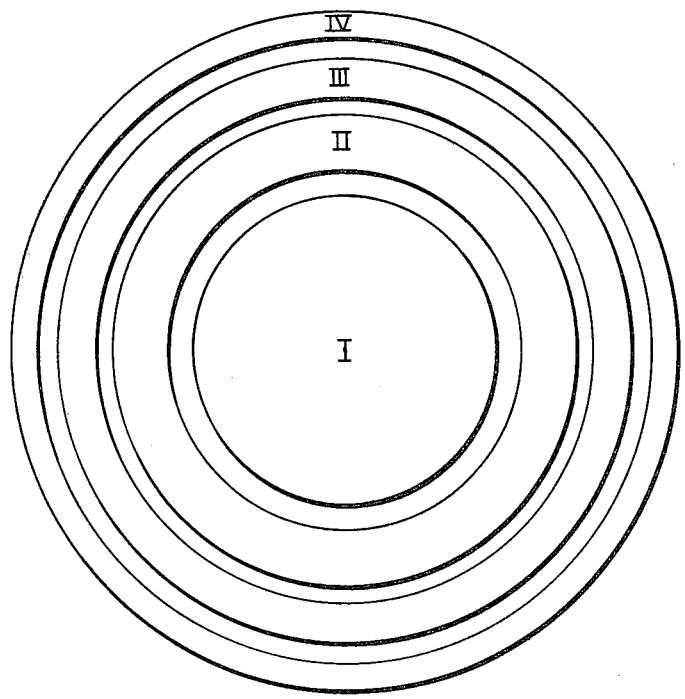
FIG. 2 is a diagram illustrating the zones of a typical zone plate used for focusing in two dimensions.

FIG. 1 illustrates the geometry for focusing in one dimension, but the same basic principle can be applied for focusing in two dimensions. The application to two dimensions of the principles illustrated in FIG. 1 is shown in FIG. 2, in which the zones of a typical zone-plate source are illustrated. Two-dimensional arrangements are advantageous in that they focus into the region of a point, not a line. It can readily be appreciated from symmetry considerations that, if the sources in FIG. 1 were uniformly radiating point sources, point P would represent a single point on a whole circle of focal points at which all of the sources would constructively interfere. In the present context, of course, in which real-world ultrasonic transducers are used, the transmission from each source is somewhat directional. Still, the energy would be focused generally in the neighborhood of a line rather than the neighborhood of a point.

In FIG. 2, four circular transducer zones I, II, III, and IV, one being disk-shaped, the rest being annular, are employed. The zones have widths, but still have the general zone-plate spacing. The resultant focus of sonic energy is on a region in the near neighborhood of a point. It should be noted that sonic energy from adjacent regions of, say, zones I and II will not be exactly in phase at the desired focal point. However, the mean distance from each transducer zone is such as to result in constructive interference, and the error resulting from the widths of the zones has not proved to be a problem as a practical matter. In fact, it has been found that relatively wide rings tend to attenuate the higher order foci that are typically produced when zone plates are used.

In the typical application of a zone plate employing this geometry, the distance to the point of focus is varied by varying the frequency of excitation of the transducer elements. By substution of c/f for $\lambda$, where c is the speed at sound in the medium and f is the excitation frequency, equation (2) yields.

$$l_o = \frac{r_n^2 f}{nc} - \frac{nc}{4f} \qquad (5)$$

Assuming $r_n \gg n\lambda$, we obtain $$l_o \cong \frac{r_n^2 f}{nc} \qquad (6)$$

Thus, the distance to the focal point is proportional to the excitation frequency, and the distance from a transducer array employing the geometry of FIG. 2 can therefore be varied electronically if a variable signal source is used.

Although focusing in the depth direction can be performed electronically in previous two-dimensional zone plates, lateral focusing has required that the angle of the transducer array be changed mechanically. According to the present invention, however, a device for electronically changing the lateral position of the focus is provided for an annular-ring-type zone plate that does not require changes in the relative phase differences between the transducer elements. According to the present invention, an array of transducer elements is provided that has the geometry shown in FIG. 3. As can be seen, the transducer of the illustrated embodiment is arranged in columns and rows of individually excitable transducer elements. In the illustrated embodiment, the dimensions of the elements in the direction of the columns varies within the column. Each column has seven elements of decreasing size as one moves out from the central element. The spacing progression will be recognized as similar to that in FIG. 1. Each row, on the other hand, consists of elements of the same size.

Such a transducer array is preferably achieved by employing any of the several known techniques for producing individually excitable transducer segments on a single chip. The same effect, of course, could be accomplished by employing discrete transducers, but the advantages in using a single-chip array are apparent. As leads 20 suggest, each of the segments is connected at the rear of the transducer to external circuitry by appropriate leads. Symmetrical pairs of segments are connected together, and as a result it would be possible for actual mechanical connections to be made only to one of a pair of symmetrical segments; those skilled in the art will recognize that an appropriate conductive strip could be provided on the chip itself to connect symmetrical pairs of transducer elements internally. Although connections are only shown as being made to the first column of transducer elements, it will be understood that similar connections are made in all of the columns.

Figure 3:
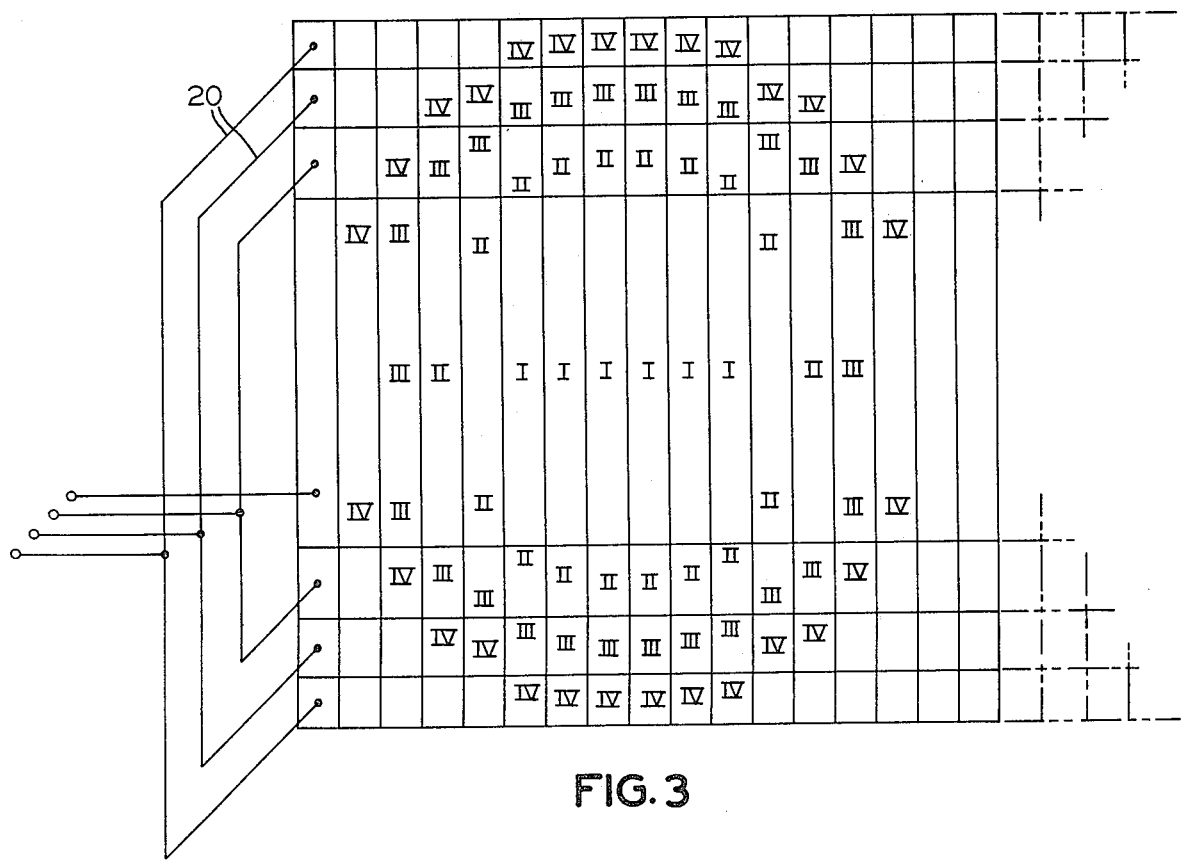
FIG. 3 illustrates the arrangements of the zones of the transducer array of the present invention.

The array shown in FIG. 3 is selectively excited so as to make it appear to have a zone-plate arrangement similar to that of FIG. 2. As was pointed out previously, the zones have widths, so that not all waves from all zones arrive exactly in phase. In fact, the zones that result in FIG. 3 are wide enough to touch each other. The general design procedure employed here was to pick a reference source, such as the central point source in FIG. 1, as providing a reference wave at the focal point. One type of zone for a phase-reversal arrangement is then a focus of adjacent points that, when in-phase sources are located at those points, produce waves that result in increased amplitude at the focal point when added to the reference wave. The other type of zone is a locus of adjacent points that would result in decreased amplitude if in-phase sources were placed at those points. Zones of one type are driven with one phase, and zones of the other type are driven with the other phase. The two types of zones, of course, alternate on the array.

It should be noted at this point that the reference source need not be located at the position shown in FIG. 1. In fact, a judicious selection of reference sources can result in a central zone that is larger than the one resulting from the reference-source location in FIG. 1. The Equation (4) relationship would still hold, although the points described by it would have relative locations within the zones that differ from those that result if the reference source were located at the very center of the zone-plate pattern.

The segments marked with roman numerals in FIG. 3 are those that are driven to achieve a specific lateral position of the focal region. All of the segments marked with the same roman numeral belong to the same zone and are excited with the same signal. The segments I all correspond to zone I of FIG. 2, and the other sements have a similar correspondence with the zones of FIG. 2. Segments I and III are excited with the same phase, while segments II and IV are excited with a signal 180° out of phase with that applied to segments I and III. This simulates the annular-ring phase-reversal zone plate and approximates its results.

Unlike prior-art two-dimensional zone plates, however, the organization of FIG. 3 can move zone-plate zones across the face of the transducer electronically. If it is desired to move the focal point in the horizontal direction in FIG. 3, it is only necessary to change the excitation of the transducer elements from that represented by the roman numerals in FIG. 3 to one that would be represented if all the roman numerals were moved in one of the directions longitudinal of the rows. As FIG. 3 indicates, the columns extend beyond those required for the zones whose excitation is represented in FIG. 3, so elements are provided that form zones that belong to a zone-plate pattern offset to the right or left from the one shown in FIG. 3. It will be appreciated that some of the transducer elements belonging to a group that provides a zone in one zone-plate pattern may also belong to a group that provides a zone in another zone-plate pattern. Accordingly, the zones may be moved across the array in one-column steps, and this would be the typical mode of lateral focusing. Thus, the benefits of the two-dimensional zone plate are provided in a device that additionally affords electronic focusing in all three spacial dimensions.

Figure 4:
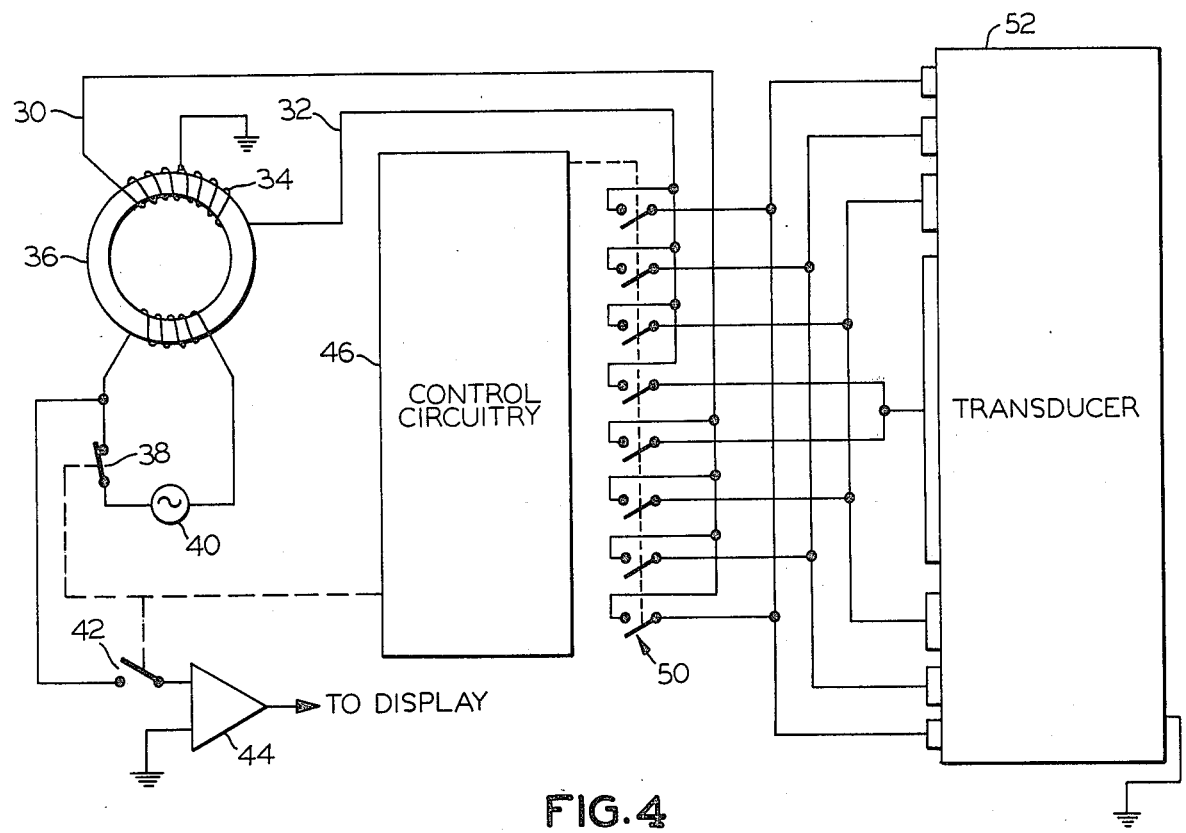
FIG. 4 is a schematic diagram of the circuitry employed to excite the transducer elements and process the signals that the transducer elements pick up.

Circuitry for realizing these functions is illustrated in FIG. 4. The transducer 52 is shown schematically in FIG. 4 as the side of a chip in which the transmitting face is to the right and the contacts made to one column of segments in the rear of the transducer are shown to the left. A bank of switches indicated by reference numeral 50 is provided. These would typically be electronic switches controllable by appropriate control circuitry 46. The control circuitry would best be provided in the form of a microprocessor, possibly with additional buffers or other ancillary circuitry.

An oscillator 40 generates a signal having a frequency, typically in the low megahertz range, that will produce a focal point at the desired distance from the transducer. The signal from oscillator 40 is applied to a transformer 36, which magnetically couples the signal from the signal generator to the secondary 34 of the transformer 36. Transformer 36 would typically be a ferrite-core transformer of the type designed for low losses at the high frequencies employed in the circuit. Although there is no reason in principle why an air-core transformer could not be employed, it is desirable from a practical standpoint that the high coupling coefficient available from ferrite-core transformers be achieved.

Secondary winding 34 of transformer 36 is center tapped as shown in the drawing to provide output parts at opposite sides of secondary 34 at which signals are present that are equal in frequency and amplitude and opposite in phase. The signal on line 30, which carries the signal from one port, is applied to one side of half of the switches 50, while the other half of the switches receives the signal on lead 32, which carries the signal from the other port. It is to be understood that the switches shown in FIG. 4 only represent those provided for a single column of the segments of FIG. 3; the number of switches shown in FIG. 4 is multiplied in the preferred embodiment by the number of columns.

Each of the switches 50 has one side connected to a transducer segment. With the exception of the two switches connected to the central segment, one side of each switch is connected to both segments of a symmetrical pair, and each transducer segment is connected to one side of two switches, one of which is connected to one output port, the other of which is connected to the other output port. The control circuitry 46 has connections for controlling all of the switches 50 and insures that at least one of the switches connected to each segment is closed at any given time. Therefore, at most one phase is applied to a given transducer segment.

The transducer elements act not only as transmitters but also as receivers, and control circuitry 46 operates switches 38 and 42 to switch the device between the transmit and receive modes. Although not so represented in FIG. 4, switches 38 and 42 would normally also be electronic switches. Switch 38 is shown closed in FIG. 4 to demonstrate the transmit mode, in which the oscillator 40 in connected through switch 38 to the transformer 36. However, during the time in which the circuitry listens for echoes, switch 38 is opened and switch 42 closed to connect oscillator 40 to the input of an amplifier 44. The amplifier output is applied to appropriate display equipment of the type known in the art. For practical reasons, oscillator 40 is normally turned off during receive times, and it would therefore be possible in principle to dispense with switch 38 (and, indeed, switch 42) as part of the means for switching between modes. However, it is thought that the illustrated arrangement will be found preferable.

In operation, control circuitry 46, which has the pattern shown in FIG. 3 stored in its memory, applies control signals to the switches in bank 50 in such a manner as to apply the proper phases to the proper segments. Initially, then, control circuitry 48 operates switch bank 50 to connect the segments so that they are excited with, for instance, the phases shown in FIG. 3. When the proper connection has been made, control circuitry 46 operates switches 38 and 42 to the transmit mode, and a short burst of high-frequency signal is transmitted through transformer 36 to the various transducer segments and out into the medium of propagation, typically a part of a patient's body. Control circuitry 46 then returns switches 38 and 42 to the receive mode after the short burst of high-frequency signal is complete, and the signals received at the various transducer segments travel through the same switches 50 through which the signals that excited the transducer segments were transmitted.

In this way, the received echoes are added in secondary 34 in the proper phase to give the device a high gain for the intended focal region. Transformer 36 therefore both provides phase splitting and also acts as a convenient way to add the signals from the various transducer segments. The resultant signal is magnetically coupled to the primary of transformer 36 and transmitted through switch 42 to amplifier 44 for transmission to display devices.

As was mentioned above, control circuitry 46 acts to sweep the focal point electronically through a linear path, and this is achieved by activating FETs in bank 50 to translate the phase pattern of FIG. 3 by one column. Subsequent actuations of the FETS wil continue the movement of the phase pattern across the face of the transducer, and the focal region will move as a result. Thus, it is possible to scan through a lateral distance determined by the length of the transducer. Furthermore, translating the focal point in range can be accomplished by varying the frequency applied by signal generator 40.

It is apparent that the foregoing disclosure will suggest a wide variety of different arrangements for employing the basic principle described here. For instance, a somewhat more complicated, but also more versatile arrangement of segments would employ equal-sized segments. It would still be possible to achieve the characteristic spacing of the zone plate, although it would take more segments for the same number of zones, and translation along two transverse axes as opposed to just one would be possible. Additionally, it could allow the size and spacing of the zones to be changed so that the range could be varied without a change in excitation frequency. As a matter of fact, the range can be varied with the FIG. 3 array without changing frequency; if zones I and II were combined into a single new zone I and zones III and IV were combined into a single new zone II, the focal length would be doubled. Of course, the results would be less satisfactory with only two zones, but this could be remedied by adding more rows to permit move zones.

It is also apparent that the concept described here is not limited to a phase-reversal zone plate. It could also be applied, for instance, to the conventional Fresnel zone plate, in which all sources are in phase. In such an arrangement, it would be necessary to space the zones by, for instance, not exciting zones II and IV because spacing between zones is necessary when all the sources are in phase. In principle, the foregoing teachings could also be applied to zone-plate arrangements in which the phase difference between the zones is other than 180° or 0°, but such devices would, of course, be somewhat more complex.

The invention and its illustrated embodiment produce several advantages over the prior art. The many advantages of the zone-plate organization are afforded in a structure that permits electronic focusing not only in depth but also in a transverse direction. This transverse motion of the focal region is afforded in a very simple and inexpensive arrangement, and, as contrasted with phased-array arrangements that also provide electronic focusing, very little memory is needed in the control circuitry. It is only necessary for the circuitry in the present invention to remember for each segment whether it is excited with one phase, excited with another phase, or unexcited, and the symmetrical organization further reduces the storage requirements. In a phased array, on the other hand, several bits of storage are needed for each element in order to store the amount of delay desired. Furthermore, the preferred embodiment includes a single transformer for providing the phases, while numerous expensive delay lines with multiple taps are necessary in a phased-array device. In addition, the transformer not only provides the phases necessary both for transmission and reception but also adds the signals from all of the segments.

Accordingly, it is thought that embodiments of the present invention will greatly advance the art by providing real-time ultrasonic imaging in a price range that will greatly enchance their availability and permit the application of ultrasonic imaging to areas in which expense previously precluded its use.

Having thus described the invention, I claim:

1. An electronically focused ultrasound transmitter comprising:

a. a transducer-element array arranged in mutually perpendicular rows and columns, said columns being provided at substantially equal intervals, said rows being provided at intervals having substantially a zone-plate progression and including first, second, third, and fourth generally circular groups of transducer elements, said first and second groups being concentric and forming a first zone-plate pattern, said third and fourth groups being concentric about a center spaced from the center of said first and second groups by a given directed distance and forming a second zone-plate pattern spaced from said first zone-plate pattern by said given directed distance, said first and third groups having no transducer elements in common with said second and fourth groups, respectively;

b. signal generator means, including first and second output ports, for generating first and second excitation signals of equal frequency and opposite phase and impressing said first and second output ports, respectively;

c. a multiplicity of switch means, each of said switch means being electrically connected between one output port and at least one transducer element associated with said switch means and being operable by application of control signals thereto to connect and disconnect each transducer element associated with it to said output port to which it is connected; and d. control circuit means, electrically connected to said switch means for application of control signals thereto, for generating control signals and applying them to said switch means to simultaneously connect said first output port to said transducer elements of said first group and said second output port to said transducer elements of said second group, thereby focusing acoustic power from said transducer elements on a first focal region, and subsequently to simultaneously connect said first output port to said transducer elements of one of said third and fourth groups and said second output port to said transducer elements of the other of said third and fourth groups, thereby focusing acoustic energy on a second focal region spaced by said given directed distance from said first focal region.

2. The electronically focused ultrasound transmitter of claim 1 wherein each column includes transducer elements whose dimensions in the direction of said column vary generally in a zone-plate progression, each row including transducer elements of substantially equal dimensions in the direction of said columns, wherein said third group of transducer elements consists of each transducer element that is disposed a predetermined number of transducer elements in a given direction along its row from a transducer element of said first group, and wherein said fourth group of transducer elements consists of each transducer element that is disposed said predetermined number of transducer elements in said given direction along its row from a transducer element of said second group.

3. The ultrasound transmitter of claim 2 wherein each of said columns includes a central transducer element and a plurality of pairs of other transducer elements, each pair being spaced symmetrically about said central transducer element, and wherein each switch electrically connected to one transducer element of a symmetrically spaced pair is also electrically connected to the other transducer element of the same pair, transducer elements of a symmetrical pair thereby being driven by the same one of said first and second excitation signals.

4. The ultrasonic transmitter of claim 3 wherein each of at least some of said transducer elements are electrically connected to two of said switch means, one of which is electrically connected to said first output port, the other of which is electrically connected to said second output port, for alternate driving by either of said first and second excitation signals.

5. The ultrasound transmitter of claim 4 wherein there are seven rows of transducer elements, each row including a central transducer element and three pairs of other transducer elements, each pair being arranged symmetrically about said central transducer element.

6. The ultrasound transmitter of claim 2, 3, 4, or 5 wherein said signal generator means includes a transformer having primary and center-tapped secondary windings and further includes an oscillator connected across said primary windings for application thereto of a signal having the desired excitation frequency, said transformer secondary windings being grounded at said center tap and thereby providing said first and second output ports at opposite ends thereof.

7. The ultrasound trasmitter of claim 6, wherein said transformer is a ferrite-core transformer.

8. The ultrasound transmitter of claim 1 wherein said signal generator means includes a transformer having a primary and center-tapped secondary windings and further includes an oscillator connected across said primary windings for application thereto of a signal having the desired excitation frequency, said transformer secondary windings being grounded at the center tap and thereby providing said first and second output ports at opposite ends of thereof.

9. The ultrasound transmitter of claim 8 further including transmission circuit means electrically connected to said primary windings for reception of signals present on said primary windings, adapted for electrical connection to display means, and operable by application of control signals thereto when electrically connected to the display means to alternately apply to and withhold from the display means signals from said primary windings, wherein said signal generator means is operable by application of control signals thereto to alternately apply to and withhold from said transformer primary windings signals from said oscillator, and wherein said control circuit means is electrically connected to said signal generator means and said transmission circuit means for application of signals thereto, said control circuit means including means for applying control signals to said transmission circuit means and said signal generator means to alternately operate said signal generator means to apply said oscillator signal to said primary windings while operating said transmission circuit means to withhold the signal on said primary windings from the display means and operate said transmission circuit means to apply the signal on said primary windings to the display means while operating said signal generator means to withhold from said primary windings signals from said oscillator.

10. The ultrasound transmitter of claim 9 wherein said transformer is a ferrite-core transformer.

11. The ultrasound transmitter of claim 1, 2, 3, 4, 5, 8, or 9 wherein some of said transducer elements included in said third or fourth group are also included in said first or second group.

12. An electronically focused ultrasound transmitter comprising:

a. a transducer-element array arranged in mutually perpendicular rows and columns, said columns being provided at substantially equal intervals, said rows being provided at intervals having substantially a zone-plate progression and including first, second, third, and fourth generally circular groups of transducer elements, said first and second groups being concentric and forming a first zone-plate pattern, said third and fourth groups being concentric about a center spaced from the center of said first and second groups by a given directed distance and forming a second zone-plate pattern spaced from said first zone-plate pattern by said given directed distance, said first and third groups having no transducer elements in common with said second and fourth groups, respectively;

b. signal generator means, including at least one output port, for generating and impressing upon each output port an excitation signal associated with said output port, each excitation signal having the same frequency;

c. a multiplicity of switch means, each of said switch means being electrically connected between one output port and at least one transducer element associated with said switch means and being operable by application of control signals thereto to connect and disconnect each transducer element associated with it to said output port to which it is connected; and d. control circuit means, electrically connected to said switch means for application of control signals thereto, for generating control signals and applying them to said switch means to simultaneously connect an output port to said transducer elements of said first group and an output port to said transducer elements of said second group, thereby focusing acoustic power from said transducer elements on a first focal region, and subsequently to simultaneously connect an output port to said transducer elements of said third group and an output port to said transducer elements of said fourth group, thereby focusing acoustic power on a second focal region spaced by said given directed distance from said first focal region.

13. A method of electronically focusing acoustic power comprising the steps of:

a. providing a transducer-element array arranged in mutually perpendicular rows and columns, said columns being provided at substantially equal intervals, said rows being provided at intervals having substantially a zone-plate progression and including first, second, third, and fourth generally circular groups of transducer elements, said first and second groups being concentric and forming a first zone-plate pattern, said third and fourth groups being concentric about a center spaced from the center of said first and second groups by a given directed distance and forming a second zone-plate pattern spaced from said first zone-plate pattern by said given directed distance, said third and fourth groups having no transducer elements in common with said first and second groups, respectively;

b. simultaneously driving said first group with a first excitation signal and said second group with a second excitation signal equal in frequency to said first excitation signal but opposite in phase, thereby concentrating acoustic power on a first focal region; and c. subsequently driving said third group with one of said first and second excitation signals and said fourth group with the other of said excitation signals, thereby concentrating acoustic power on a second focal region spaced by said given directed distance from said first focal region.

* * * * *

UNITED STATES PATENT AND TRADEMARK OFFICE
CERTIFICATE OF CORRECTION

PATENT NO. : 4,307,613
DATED : December 29, 1981
INVENTOR(S) : Martin D. Fox

It is certified that error appears in the above—identified patent and that said Letters Patent is hereby corrected as shown below:

Column 11, line 4, after "second" insert -- excitation signals on said first and second --.

Signed and Sealed this

Fifth Day of October 1982

[SEAL]

Attest:

Attesting Officer

GERALD J. MOSSINGHOFF
Commissioner of Patents and Trademarks